(12) United States Patent  
Matsui et al.

(10) Patent No.: US 7,719,669 B2
(45) Date of Patent: May 18, 2010

(54) SURFACE INSPECTION METHOD AND SURFACE INSPECTION APPARATUS

(75) Inventors: Shigeru Matsui, Hitachinaka (JP); Masayuki Hachiya, Tokorozawa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 279 days.

(21) Appl. No.: 11/776,912

(22) Filed: Jul. 12, 2007

(65) Prior Publication Data

US 2008/0013084 A1 Jan. 17, 2008

(30) Foreign Application Priority Data

Jul. 13, 2006 (JP) ............................. 2006-193184

(51) Int. Cl.
 *G01N 21/88* (2006.01)
(52) U.S. Cl. .................. 356/237.1; 356/237.3
(58) Field of Classification Search ... 356/237.2–237.5, 356/614–622
See application file for complete search history.

(56) References Cited

U.S. PATENT DOCUMENTS

| | | | | |
|---|---|---|---|---|
| 5,798,829 A | | 8/1998 | Vaez-Iravani | |
| 6,157,444 A | * | 12/2000 | Tomita et al. | 356/237.1 |
| 6,226,079 B1 | * | 5/2001 | Takeda et al. | 356/237.2 |
| 6,288,780 B1 | * | 9/2001 | Fairley et al. | 356/237.1 |
| 6,774,991 B1 | * | 8/2004 | Danko | 356/237.4 |
| 7,463,349 B1 | * | 12/2008 | Biellak et al. | 356/237.2 |
| 7,487,049 B2 | * | 2/2009 | Matsui | 702/40 |
| 2001/0015802 A1 | * | 8/2001 | Tomita et al. | 356/237.2 |
| 2006/0152716 A1 | * | 7/2006 | Meeks | 356/237.2 |
| 2008/0013076 A1 | * | 1/2008 | Matsui | 356/73 |
| 2008/0174764 A1 | * | 7/2008 | Matsui | 356/73 |
| 2009/0033924 A1 | * | 2/2009 | Uto et al. | 356/237.2 |
| 2009/0066941 A1 | * | 3/2009 | Togashi et al. | 356/237.3 |

FOREIGN PATENT DOCUMENTS

| | | |
|---|---|---|
| JP | 11-223607 A | 8/1999 |
| JP | 2001-235431 A | 8/2001 |
| JP | 2001-255278 A | 9/2001 |

* cited by examiner

*Primary Examiner*—Hoa Q Pham
(74) *Attorney, Agent, or Firm*—Crowell & Moring LLP

(57) ABSTRACT

Light from a light source becomes two illumination beams by a beam splitter. The beams are irradiated onto a semiconductor wafer from two mutually substantially orthogonal azimuthal angles having substantially equal elevation angles to form illumination spots. When the sum of scattered, diffracted, and reflected lights due to the illumination beams is detected, influence of the anisotropy which a contaminant particle and a defect existing in the wafer itself or thereon have with respect to an illumination direction, can be eliminated.

20 Claims, 13 Drawing Sheets

OPTICAL AXIS OF SPECULAR REFLECTION LIGHT BY 21 AND 21

OPTICAL AXIS OF SPECULAR REFLECTION LIGHT BY 22 AND 22

SURFACE INSPECTION METHOD AND SURFACE INSPECTION APPARATUS

BACKGROUND OF THE INVENTION

1. Field of the Invention

The present invention relates to a surface inspection method which measures information on a minute contaminant particle and a defect on a semiconductor substrate (semiconductor wafer), and surface roughness of the substrate.

2. Description of the Related Art

In a production line for semiconductor substrates (semiconductor wafers), inspection for defects such as a contaminant particle attached to the surface of the semiconductor substrate and a scratch generated during processing is performed in order to observe a state where dust is generated in a manufacturing apparatus. For example, in the semiconductor substrate before forming a circuit pattern, a minute contaminant particle and a defect not larger than several 10 nm on the surface thereof need to be detected. Furthermore, a crystal defect existing in a shallow region adjacent to the substrate surface and surface roughness of the substrate surface are also become inspection objects other than the contaminant particle and the defect as the inspection of the surface of the semiconductor substrate.

As for technology for detecting a minute defect on the surface of an object to be inspected such as a semiconductor substrate, for example, as disclosed in U.S. Pat. No. 5,798,829, a focused laser luminous flux is irradiated onto the surface of the semiconductor substrate; scattered light generated in the case where a contaminant particle is attached to the semiconductor substrate is detected; and a contaminant particle and a defect on the entire surface of the semiconductor substrate are inspected by rotation and translation feed of the semiconductor substrate.

It is configured such that an ellipsoidal mirror is used for detecting scattered light, a detection position on the semiconductor substrate is set to a primary focus position of an ellipse, and the light receiving surface of a light receiving element is arranged on a secondary focus position; and accordingly, the scattered light generated at the contaminant particle can be collected with a wide solid angle, and a minute contaminant particle can also be detected.

In the technology disclosed in U.S. Pat. No. 5,798,829, a laser luminous flux which is for illuminating the semiconductor substrate includes both oblique illumination and normal illumination with respect to an elevation angle to the substrate surface; however, only an illumination luminous flux from only one azimuthal angle is provided with respect to one elevation angle.

In addition, for example, as disclosed in Japanese Patent Application Laid-Open No. 2001-255278, there is provided one in which a condenser lens and a photodetector are arranged at a position where a plurality of elevation angles and a plurality of azimuthal angles are combined with respect to the surface of a semiconductor substrate, and scattered light focused by each condenser lens is detected by the photodetector; and accordingly, detection in an advantageous direction can be enabled in accordance with three-dimensional irradiation distribution characteristics of the scattered light from a minute contaminant particle.

Also in the technology disclosed in Japanese Patent Application Laid-Open No. 2001-255278, a laser luminous flux which is for illuminating the semiconductor substrate includes two oblique illumination and normal illumination; however, only one azimuthal angle of the laser luminous flux corresponding to one incident angle (elevation angle) is provided.

Furthermore, in Japanese Patent Application Laid-Open No. 2001-235431, technology which uses two laser light sources having different wavelengths for a light source; and in this technology, illumination light from two laser light sources are incident to the surface of the semiconductor substrate from the same azimuthal angles but with different incident angles, that is, with different elevation angles.

In addition, in the technology disclosed in Japanese Patent Application Laid-Open No. 11-223607, technology in which the surface of the semiconductor substrate is illuminated at different two azimuthal angles from substantially the same elevation angles using two laser light sources having different wavelengths; however, the two azimuthal angles in this case have mutually different directions by 180°, and two illumination regions have a relation in parallel with each other.

In the above prior art, if illumination is performed from one azimuthal angle, as generally shown in FIG. 15, an illumination beam 21 is incident to an irradiation region on the semiconductor wafer along a direction of a straight line which connects the illumination region to the rotational center of rotation operation that is primary scan of a movement stage for an object to be inspected. In this case, as shown in FIG. 16, an (x, y) coordinate system fixed on the surface of the semiconductor wafer having a cutout portion 300 whose crystal orientation can be identified, is taken.

When the semiconductor wafer is rotationally moved and illuminated by the illumination beam 21 from a fixed direction, a point A on the semiconductor wafer is illuminated from a direction in parallel with a y-axis of the (x, y) coordinate system; however, a point B is illuminated from a direction in parallel with an x-axis. In addition, a point C is illuminated from a direction making 45° with the x-axis and the y-axis, which is at a position intermediate therebetween.

In the case where a contaminant particle and a defect having such an anisotropy that depends on an incidence direction of the illumination light are attached to the surface of the semiconductor wafer, intensity of the scattered light generated by the illumination light differs according to which position on the semiconductor wafer the contaminant particle or the like is attached to. Therefore, it is to be expected that there generates a difference in detection sensitivity and there arises an error when the size of the contaminant particle and the defect are calculated on the basis of the scattered light intensity.

In addition, in a semiconductor wafer polished to extremely enhance flatness of the surface, there appears surface roughness having a level close to an atomic arrangement step which constitutes the surface thereof; however, and such arrangement step generally appears having a large correlation with crystal orientation of the semiconductor wafer. Therefore, if the same position of such semiconductor wafer is illuminated from the same elevation angle with different azimuthal angle; scattered light having different intensity is generated.

That is, if such semiconductor wafer is illuminated by illumination light from different directions by the rotational movement, even in the case where the entire surface of the semiconductor wafer has uniform surface roughness, scattered light which differs in its intensity for each rotation angle with the primary scan rotation of the movement stage for the object to be inspected is observed. This often occurs in an actual surface inspection apparatus, and intensity distribution on the semiconductor wafer of a signal derived from the surface roughness of the semiconductor wafer (referred to as "haze signal" below) often becomes as shown in FIG. 17, for example.

FIG. 17 shows that the haze signal is large in the order of a→b→c→d→e→f→g. The anisotropy of detection sensitivity of the haze signal has an influence on also the detection sensitivity of the contaminant particle and the defect. That is, it is well known that a noise level at the time of detecting the scattered light from the contaminant particle and the defect depends on fluctuation (shot noise) of the scattered light derived from the surface roughness, and a threshold at the time of detecting a signal from the contaminant particle and the defect needs to be increased at a portion where the haze signal is high; and as a result, the detection sensitivity of the contaminant particle and the defect decreases.

SUMMARY OF THE INVENTION

An object of the present invention is to realize a surface inspection method and a surface inspection apparatus capable of inspecting a contaminant particle and a defect, or surface roughness with a uniform sensitivity without depending on a rotation angle in a primary scan direction, even in the case where intensity of scattered light, which is generated derived from a contaminant particle and a defect existing on the surface of a semiconductor wafer or adjacent to the surface, or surface roughness of the semiconductor wafer, has anisotropy which depends on an illumination direction.

According to one aspect of the present invention, there is provided a surface inspection method which irradiates an optical beam onto the surface of an object to be inspected mounted on a movement stage for the object to be inspected in which primary scan is performed by rotational movement and secondary scan is performed by translation movement; collects scattered, diffracted, and reflected lights from the object to be inspected; and inspects the surface of the object to be inspected on the basis of the collected light.

Then, the surface inspection method includes the steps of irradiating two optical beams from mutually different azimuthal angles at substantially the same elevation angles with respect to the surface of the object to be inspected onto two regions different in the surface of the object to be inspected; collecting scattered, diffracted, and reflected lights from the two regions; and detecting the position and the size of a contaminant particle and a defect existing on the surface of the object to be inspected or in the inside adjacent to the surface, or surface roughness of the object to be inspected on the basis of the collected light.

In addition, according to another aspect of the present invention, there is provided a surface inspection apparatus which includes a movement stage for an object to be inspected in which primary scan is performed by rotational movement and secondary scan is performed by translation movement; a unit which irradiates an optical beam onto the surface of the object to be inspected mounted on the stage; a unit which collects scattered, diffracted, and reflected lights from the object to be inspected; and an inspection unit which inspects the surface of the object to be inspected on the basis of the collected light.

Then, the surface inspection apparatus includes an optical beam irradiating unit which irradiates two optical beams from mutually different azimuthal angles at substantially the same elevation angles with respect to the surface of the object to be inspected onto two regions different in the surface of the object to be inspected; a condenser unit which collects scattered, diffracted, and reflected lights from the two regions; and a detecting unit which detects the position and the size of a contaminant particle and a defect existing on the surface of the object to be inspected or in the inside adjacent to the surface, or surface roughness of the object to be inspected on the basis of the collected light.

It is possible to realize a surface inspection method and a surface inspection apparatus capable of inspecting a contaminant particle and a defect, or surface roughness with a uniform sensitivity without depending on a rotation angle in a primary scan direction, even in the case where intensity of scattered light generated derived from a contaminant particle and a defect existing on the surface of a semiconductor wafer or adjacent to the surface, or surface roughness of the semiconductor wafer has anisotropy which depends on an illumination direction.

The embodiments of the present invention will be described below with reference to the accompanying drawings.

DESCRIPTION OF THE PREFERRED EMBODIMENTS

Figure 1:
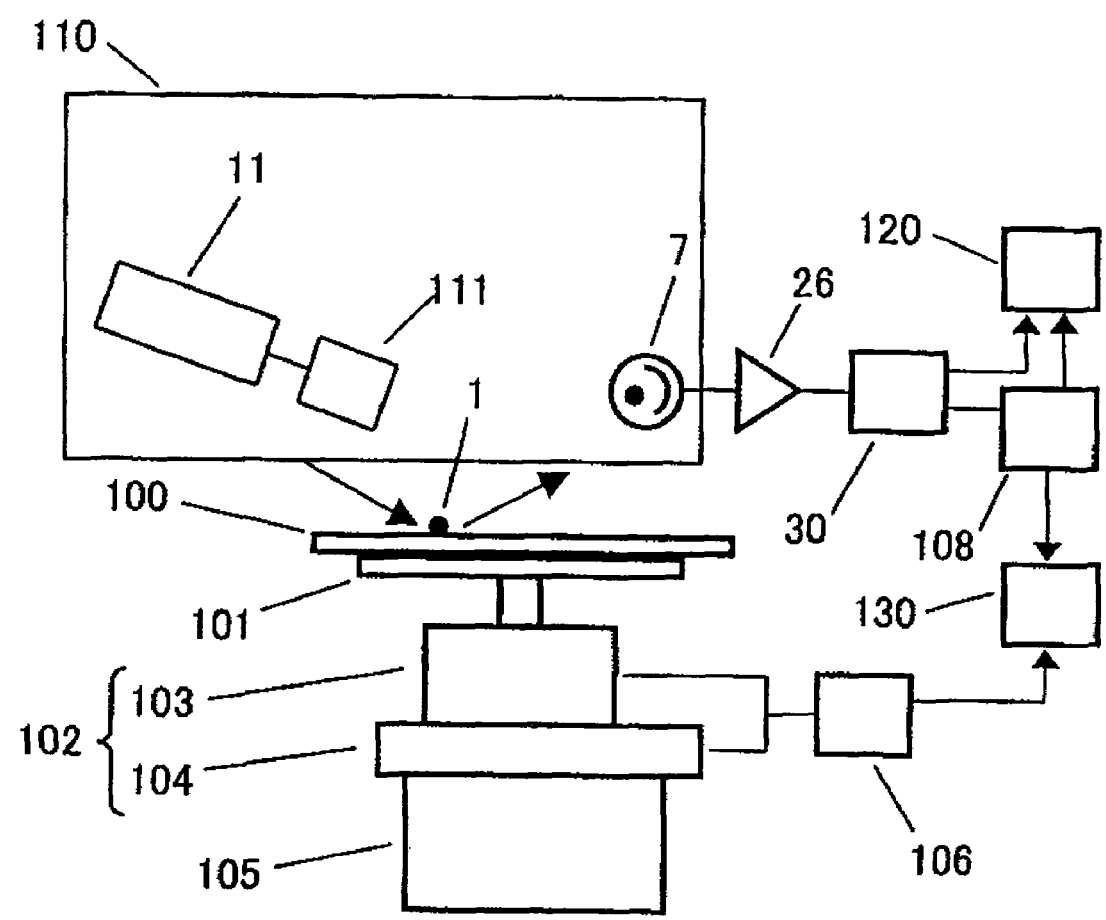
FIG. 1 is a schematic configuration view of a contaminant particle and defect inspection apparatus according to a first embodiment of the present invention.

FIG. 1 is a schematic configuration view of a contaminant particle and defect inspection apparatus according to a first embodiment of the present invention. In FIG. 1, a semiconductor wafer 100 that is an object to be inspected is vacuum-contacted to a chuck 101, and the chuck 101 is mounted on a movement stage for an object to be inspected 102 provided with a rotation stage 103 and a translation stage 104, and a Z stage 105.

Figure 2:
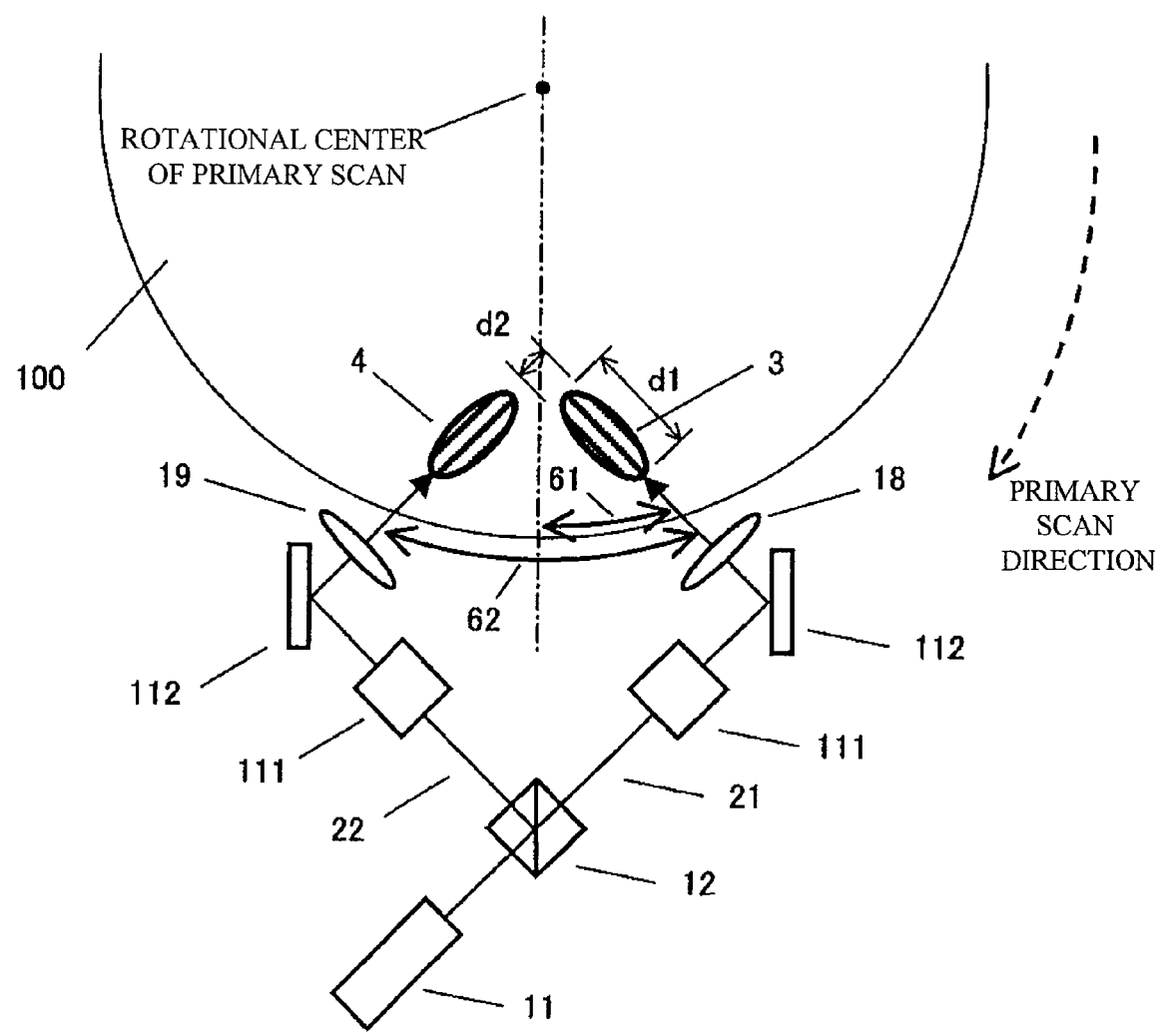
FIG. 2 is a plan view of illumination and detection optics arranged above a semiconductor wafer of the contaminant particle and defect inspection apparatus according to the first embodiment of the present invention.
Figure 3:
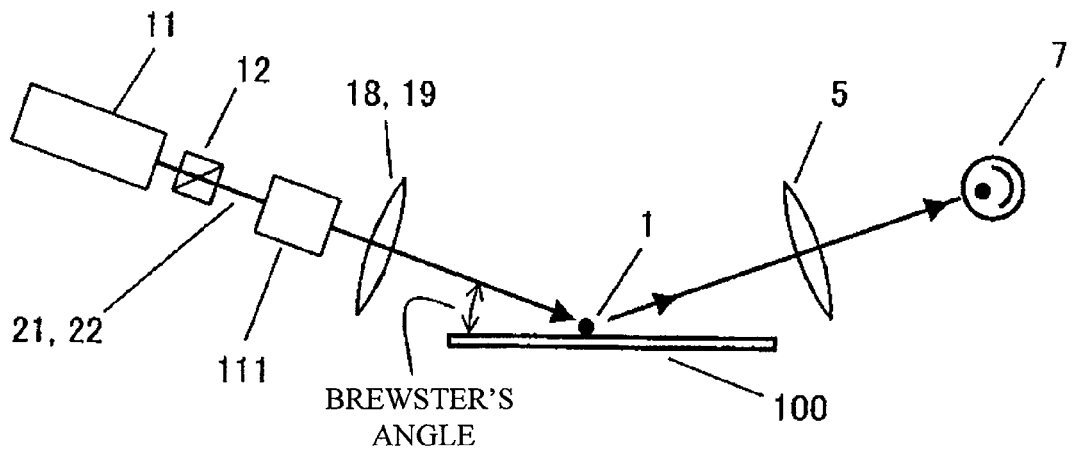
FIG. 3 is a side view of the illumination and detection optics arranged above the semiconductor wafer of the contaminant particle and defect inspection apparatus according to the first embodiment of the present invention.

Illumination and detection optics 110 arranged above the semiconductor wafer 100 are optics shown in FIG. 2 and FIG. 3. FIG. 2 is a plan view of the optics, and FIG. 3 is a side view of the optics.

In FIG. 2 and FIG. 3, a light source 11 of illumination light in the illumination and detection optics 110 uses a pulse laser which performs pulse oscillation by time repeating light of a wavelength in a UV region. The light outputted from the light source 11 is divided into two illumination beams 21 and 22 by a beam splitter 12.

Figure 4:
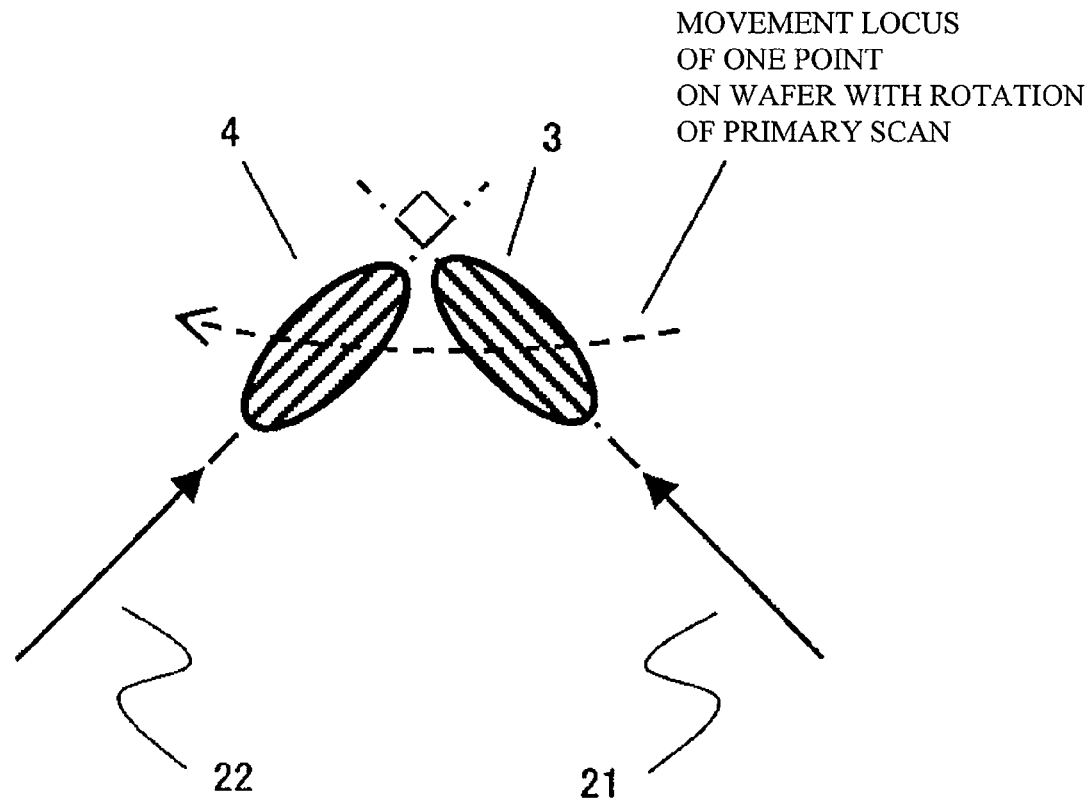
FIG. 4 is a principle explanation view of the contaminant particle and defect inspection apparatus according to the first embodiment of the present invention.

The illumination beam 21 reaches an irradiation lens 18 via a polarization control unit 111 and a loopback mirror 112, and forms an illumination spot 3 shown in FIG. 4 by the function of the irradiation lens 18. In addition, the illumination beam 22 reaches an irradiation lens 19 via the polarization control unit 111 and the loopback mirror 112, and forms an illumination spot 4 shown in FIG. 4 by the function of the irradiation lens 19. The illumination spots 3 and 4 are adjusted so as not to be overlapped with each other in a primary scan direction of the movement stage for the object to be inspected 102.

In order to detect a minute contaminant particle and a minute defect with high sensitivity, it is preferable that an elevation angle of the illumination beam with respect to the surface of an object to be inspected is set to be a low elevation angle of approximately 5° to 25°, and more preferably, adjacent to Brewster's angle with respect to a material which constitutes the object to be inspected. Consequently, the first preferred embodiment of the present invention is configured such that both the illumination beams 21 and 22 are offered in oblique incidence at approximately Brewster's angle for crystal Si and both along directions from the outer circumference to the inner circumference of the semiconductor wafer 100.

Therefore, the illumination spots 3 and 4 are formed in a substantially elliptical shape. In this case, the inside of a profile line in which illuminance is reduced to one over e squared (e is base of natural logarithm) of the center portion of the illumination spot is defined again as the illumination spot. As shown in FIG. 2, the width of a major axis direction of the illumination spot is set to d1, and the width of a minor axis direction is set to d2. The illumination spots 3 and 4 have mutually substantially the same d1 and d2, and are illuminated with substantially the same illuminance.

Polarization states of both the illumination beams 21 and 22 are controlled by the polarization control unit 111 when incident to the illumination spots 3 and 4, to be "both P polarization," "both S polarization," "both circular polarization," or "both elliptical polarization having substantially equivalent ellipticity."

As shown in FIG. 2, an azimuthal angle of the illumination beam 21 to be irradiated to the semiconductor wafer 100 is disposed at an angle of an angle 61 of approximately 45° with respect to a line segment which connects the rotational center of the primary scan of the movement stage for the object to be inspected 102 to an intersection of extended lines in the major axis direction of the illumination spots 3 and 4. In addition, an azimuthal angle of the illumination beam 22 to be irradiated to the semiconductor wafer 100 is disposed at an angle of an angle 62 of approximately 90° with respect to the azimuthal angle of the illumination beam 21.

For this reason, the major axes of the illumination spots 3 and 4 are disposed at an angle of approximately 90° with respect to each other. By this arrangement, with the rotation of the primary scan of the movement stage for the object to be inspected 102, a locus depicted on the surface of the semiconductor wafer 100 by the illumination spot 3 and a locus depicted by the illumination spot 4 substantially overlap in the radius direction of the movement stage for the object to be inspected 102.

A condenser lens 5 shown in FIG. 3 has a configuration capable of collecting scattered, diffracted, and reflected lights with a low elevation angle so as to efficiently capture scattered light with respect to a minute contaminant particle which follows Rayleigh scattering. In this configuration, the contaminant particle 1 passes through the first illumination spot 3, and then, passes through the second illumination spot 4; and therefore, scattered, diffracted, and reflected light signals can be obtained two times from a photodetector 7. In addition, in the first embodiment of the present invention, a photomultiplier is used as the photodetector 7; however, a photodetector based on another detection principle may be used provided that it is a photodetector which can detect the scattered, diffracted, and reflected lights from the contaminant particle with high sensitivity.

The scattered, diffracted, and reflected light signals from the photodetector 7 are amplified by an amplifier 26, and then, sampled at every predetermined sampling interval dT by an A/D converter 30, and converted to digital data. The sampling interval dT is set to be sufficiently small with respect to a time interval from when the contaminant particle 1 passes through the illumination spot 3 to when the contaminant particle 1 passes through the illumination spot 4.

The digital data at every sampling interval dT is compared with a predetermined detection threshold by a contaminant particle and defect determination mechanism 108; and if the digital data is not lower than the threshold, the contaminant particle and defect determination mechanism 108 determines that the digital data is based on a contaminant particle and a defect, and generates contaminant particle and defect determination information.

In addition, the contaminant particle and defect determination may determine by comparing output electrical signal from the amplifier 26 with a predetermined threshold, in place of determining the presence of the contaminant particle and the defect by comparing the digital data obtained from the A/D converter 30 with the predetermined threshold voltage. If the predetermined threshold is suitably set with respect to a noise level; the scattered, diffracted, and reflected light signals, which are generated two times in total when the contaminant particle 1 passes through the illumination spot 3 and the illumination spot 4, can be correctly captured as a digital data group.

A contaminant particle and defect coordinate detection mechanism 130 calculates a coordinate position (r, θ) in a primary scan direction and a secondary scan direction of the contaminant particle and the defect from present position information of the primary scan and the secondary scan which the movement stage for the object to be inspected 102 generates when the contaminant particle and defect determination information is generated. At this time, the contaminant particle and defect coordinate detection mechanism 130 calculates the r coordinate of the coordinate position (r, θ) with further high accuracy by using the digital data group of the scattered, diffracted, and reflected light signals generated two times.

More specifically, a time interval between the scattered, diffracted, and reflected light signals generated two times is calculated; and which radius positions of the illumination spots 3 and 4 have been passed through by the contaminant particle 1 is calculated from this time interval.

In the case of an arrangement shown in FIG. 4, this uses the fact that which radius positions of the respective illumination spots 3 and 4 are passed through by the contaminant particle 1 is proportional to the time interval, such as that a time from when the contaminant particle 1 on the surface of the semiconductor wafer 100 passes through the illumination spot 3 to when the contaminant particle 1 passes through the illumination spot 4 is shorter in the case where the contaminant particle 1 is placed nearer to the rotation axis of the primary scan, and the time is longer in the case where the contaminant particle 1 is placed farther from the rotation axis of the primary scan.

At this time, the minimum obtainable value and the maximum obtainable value of the above time interval are determined by linear velocity at the time when the contaminant particle 1 passes through the illumination spots 3 and 4. In the case where the movement stage for the object to be inspected 102 is scanned at a constant linear velocity by coordination control of the primary scan and the secondary scan, the minimum value and the maximum value are constant values irrespective of radius positions during scanning; however, in the case of scanning at a constant rotational velocity, the minimum value and the maximum value are different according to the radius positions during scanning.

Therefore, the contaminant particle and defect coordinate detection mechanism 130 also uses present position information in the secondary scan (r) direction which the movement stage for the object to be inspected 102 generates, when calculating which radius position of the illumination spots 3 and 4 have been passed through by the contaminant particle 1 from the above time interval.

In this case, in order to obtain a position coordinate of the contaminant particle and the defect with high accuracy, it can be considered to obtain the coordinate of the contaminant particle and the defect from data of a plurality of laps obtained both by reducing an amount of secondary scan movement between adjacent primary scans for two laps and by overlapping the respective scan loci of the primary scan at a constant ratio.

However, as described above in the first embodiment of the present invention, the coordinate of the contaminant particle and the defect can be obtained with high accuracy using only primary scan data for one lap, it is not necessary to overlap the respective scan loci of the primary scan at a constant ratio, and the amount of secondary scan movement between adjacent primary scans for two laps can be increased; and therefore, there is an advantage that detection speed can be increased.

In addition, in the first embodiment of the present invention, accuracy with which a passing position of the contaminant particle 1 in the illumination spot is obtained does not depend on the shape of illuminance distribution in the illumination spot; and therefore, it is possible to be substantially a constant illuminance distribution in the illumination spot so as to be more advantageous to maintain detection sensitivity of the contaminant particle and the defect constant.

If the coordinate position of the detected contaminant particle and defect is obtained; and subsequently, the particle size calculating mechanism 120 calculates the size of the detected contaminant particle and defect from a digital data group.

More specifically, a signal corresponding to the sum of scattered, diffracted, and reflected light signals which are generated two times when the contaminant particle 1 passes through the illumination spot 3 and the illumination spot 4 is calculated from the digital data group, to be total scattered, diffracted, and reflected light signal; and the intensity of the total scattered, diffracted, and reflected light signal is converted into the size of the contaminant particle 1.

As described above, according to the first embodiment of the present invention, when the surface of the object to be inspected is illuminated by two illumination beams 21 and 22 from two mutually substantially orthogonal azimuthal angles having substantially equivalent elevation angles, and the sum of scattered, diffracted, and reflected lights due to both illumination lights is detected; and accordingly, influence of anisotropy which a contaminant particle and a defect existing in the object to be inspected itself or thereon have with respect to an illumination direction can be eliminated or reduced.

In addition, in the above described example, detection of the contaminant particle and the defect is described; however, it is obvious that the same effect can be obtained also in the case when surface roughness of the semiconductor wafer 100 that is an inspection object is measured.

In addition, in the above described example, the light source 11 uses "a pulse laser which performs pulse oscillation by time repeating light of a wavelength in a UV region"; however, "a laser of a wavelength other than the UV region" may be used; and the above technology can be directly used also in the case where "a continuously oscillating laser" is used in the light source.

In addition, light generated from one laser light source is divided into two illumination beams; however, two illumination beams may be generated using two separate laser light sources having substantially equal oscillation wavelengths. Similarly, directions in which two illumination beams illuminate the surface of the semiconductor wafer 100 are "both directions toward substantially from the outer circumference to the inner circumference"; however, the above technology can be directly used even in the case of "both directions toward substantially from the inner circumference to the outer circumference."

In oblique illumination, generally, there arises a phenomenon that an illumination spot position shifts when a height relationship between an illumination beam and the surface to be illuminated is changed. However, illumination directions of two illumination beams are set to "both directions toward substantially from the outer circumference to the inner circumference" and "both directions toward substantially from the inner circumference to the outer circumference," accordingly, in such case, two illumination spots 3 and 4 move on the surface of the semiconductor wafer 100 in the same directions of the radius direction by the same distance; and therefore, there can be obtained an advantage that the relationship of "along with the rotation of the primary scan of the movement stage for the object to be inspected 102, a locus depicted on the surface of the semiconductor wafer 100 by the illumination spot 3 and a locus depicted by the illumination spot 4 substantially overlap in the radius direction of the movement stage for the object to be inspected 102" is maintained without crumbling.

In the above described first embodiment of the present invention, a detection direction of the scattered, diffracted, and reflected lights is one; however, it is possible to detect the scattered, diffracted, and reflected lights from a plurality of azimuth directions by arranging photodetectors in a plurality of directions in which a plurality of elevation angles and a plurality of azimuthal angles are combined.

Figure 5:
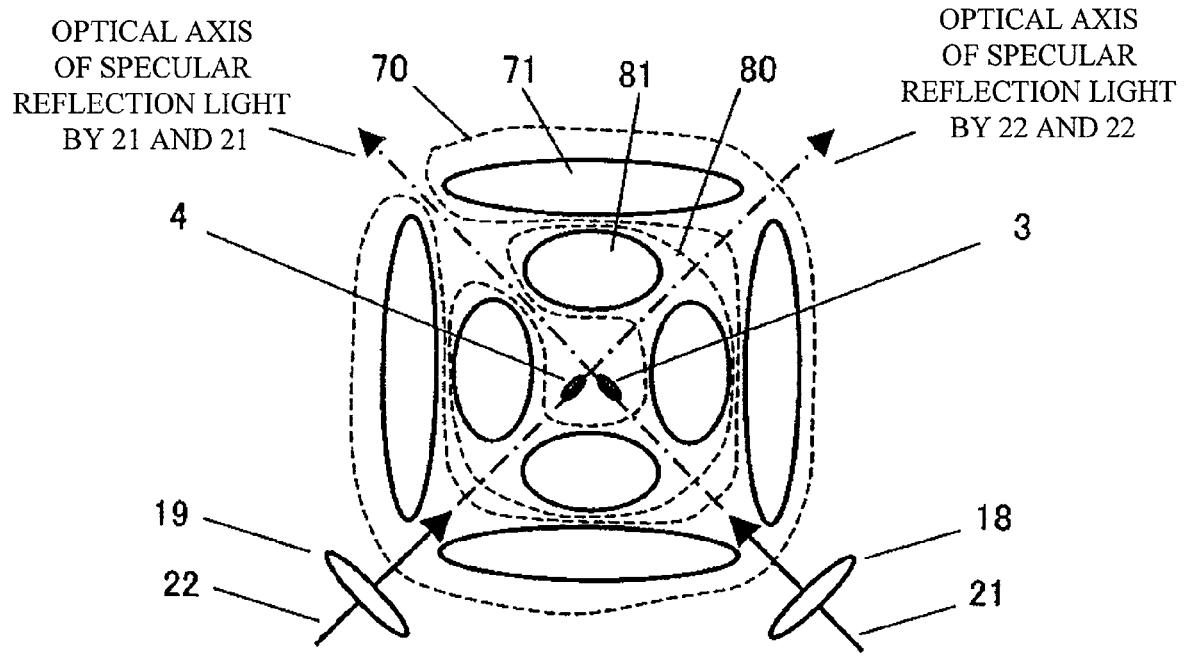
FIG. 5 is a plan view of detection optics according to a second embodiment of the present invention.
Figure 6:
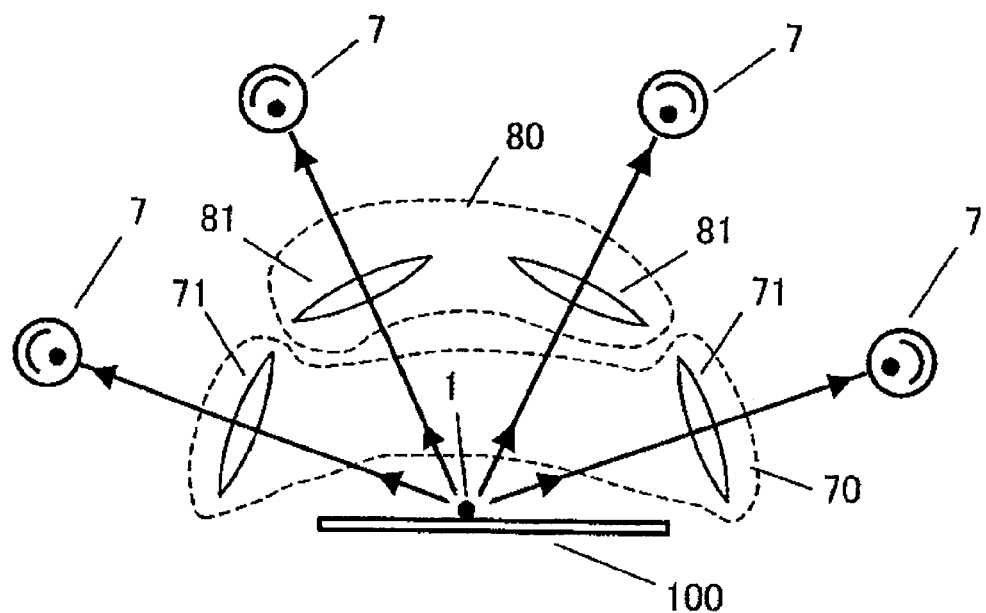
FIG. 6 is a side view of the detection optics according to the second embodiment of the present invention.

FIG. 5 and FIG. 6 are explanation views of detection optics of a second embodiment of the present invention, and showing an example which detect scattered, diffracted, and reflected lights from a plurality of azimuth directions by arranging detection optics in a plurality of directions in which a plurality of elevation angles and a plurality of azimuthal angles are combined. In addition, FIG. 5 is a plan view of the detection optics; and FIG. 6 is a side view of the detection optics.

Illumination optics in the second embodiment of the present invention is equivalent to the first embodiment, and therefore their explanation will not be described herein.

A detection system of scattered, diffracted, and reflected lights in the second embodiment of the present invention includes a first elevation angle detection system 70 including four condenser elements 71 which have first substantially equal elevation angles, differ each other with respect to a primary scan rotation axis of a movement stage for an object to be inspected 102, and detect scattered, diffracted, and reflected lights from four azimuthal angles being mutually spaced apart by approximately 90°; and a second elevation angle detection system 80 including four condenser elements 81 which have second substantially equal elevation angles larger than the first elevation angles, differ each other with respect to the primary scan rotation axis of the movement stage for an object to be inspected 102, and detect scattered, diffracted, and reflected lights from four azimuthal angles being mutually spaced apart by approximately 90°. Each of the eight condenser elements 71 and 81 is made of a lens.

Illumination light in the second embodiment of the present invention is equivalent to the first embodiment, and two illumination beams are irradiated to the surface of a semiconductor wafer 100 from a low elevation angle. Since the azimuthal angles of these two illumination beams are in mutually substantially orthogonal relationship, their specular reflection lights are also orthogonal. Therefore, there exist four optical beams to which two illumination beams and two specular reflection lights are totaled, in a relationship mutually spaced by approximately 90°. There is an apprehension that the respective condenser elements 71 and 81, especially the respective condenser elements 71 in the first elevation angle detection system, interfere with these four optical beams, in view of their mechanical arrangement.

Therefore, in the second embodiment of the present invention, these four respective condenser elements 71 and 81 are arranged avoiding optical paths of the four optical beams. More specifically, as shown in FIG. 5, respective optical axes of the four condenser elements belonging to the same elevation angles are arranged in four directions of the front right side 45°, the front left side 45°, the rear right side 45°, and the rear left side 45° by reference to an illumination beam 21.

Figure 7:
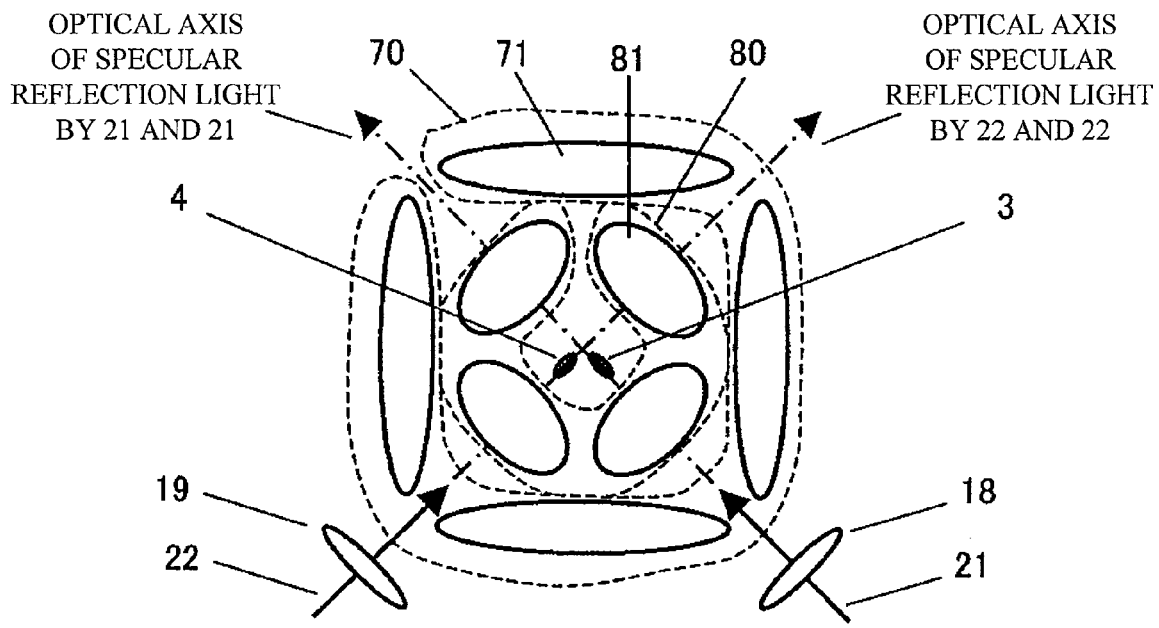
FIG. 7 is a plan view of a modified example according to the second embodiment of the present invention.

This arrangement makes it possible to effectively detect the scattered, diffracted, and reflected lights without interfering with optical paths of two illumination beams and their resultant two specular reflection lights. At this time, in the second elevation angle detection system 80 located at higher elevation angle position, when there is no apprehension to interfere with the optical paths of the four optical beams, only the first elevation angle detection system 70 can be configured to avoid the optical paths of the four optical beams as shown in FIG. 7.

Figure 8:
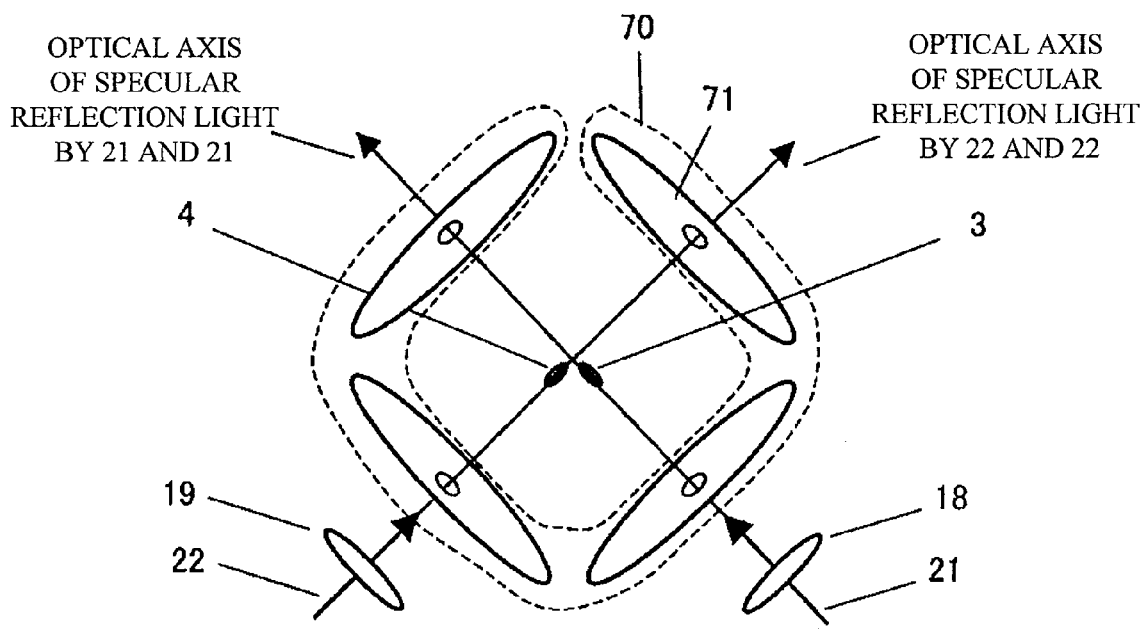
FIG. 8 is a plan view of a modified example according to the second embodiment of the present invention.
Figure 9:
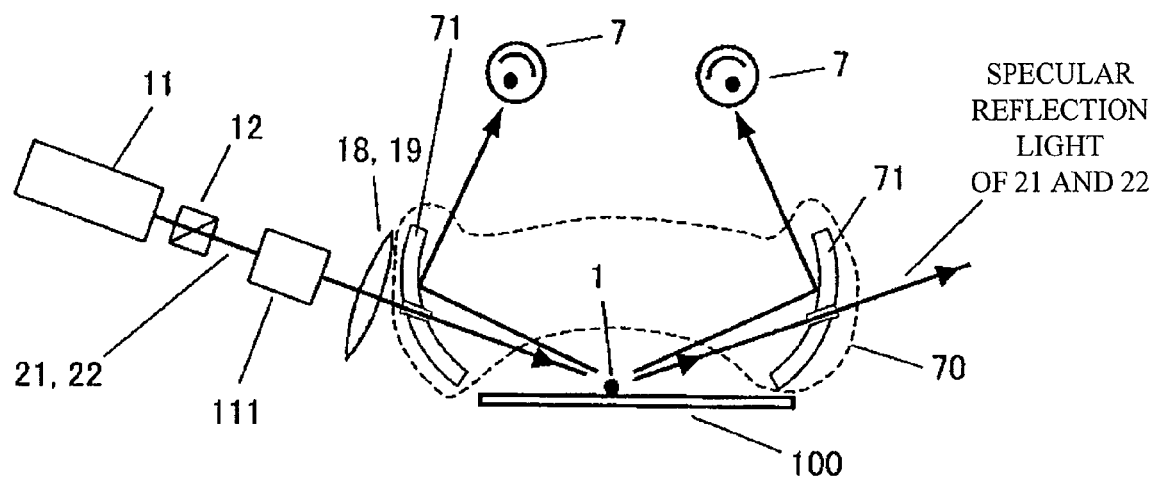
FIG. 9 is a side view of the modified example according to the second embodiment of the present invention.

In the above second embodiment, each of the condenser elements in the scattered, diffracted, and reflected light detection system are made of a lens; however, these can be made of a concave mirror. In the case where the concave mirrors are used in the condenser elements, of course, the respective optical axes of the concave mirrors can be arranged to avoid the optical paths of the four optical beams as in the above case; however, as shown in FIGS. 8 and 9, the respective optical axes of the four condenser elements 71 belonging to the same elevation angles can be arranged in four directions of substantially the front, the left side, the right side, and the rear by reference to the illumination beam 21. At this time, the respective mirror planes interfere with the optical paths of the two illumination beams and their resultant two specular reflection lights; however, such optical interference can be avoided by forming through holes in the respective mirror planes so that the optical beams pass through.

As described above, according to the second embodiment of the present invention, similar effect as in the first embodiment can be obtained, and in addition to that, two scattered, diffracted, and reflected light signals measured from two different elevation angles with respect to one contaminant particle and defect can be obtained; and therefore, a contaminant particle and defect determination mechanism 108 compares a first and a second combined scattered, diffracted, and reflected light signals, and can discriminate a type of the detected contaminant particle and defect, for example, whether the detected one is an attached contaminant particle on the surface of the semiconductor wafer 100, or a crystal defect inside the semiconductor wafer 100, and classify them.

Figure 10:
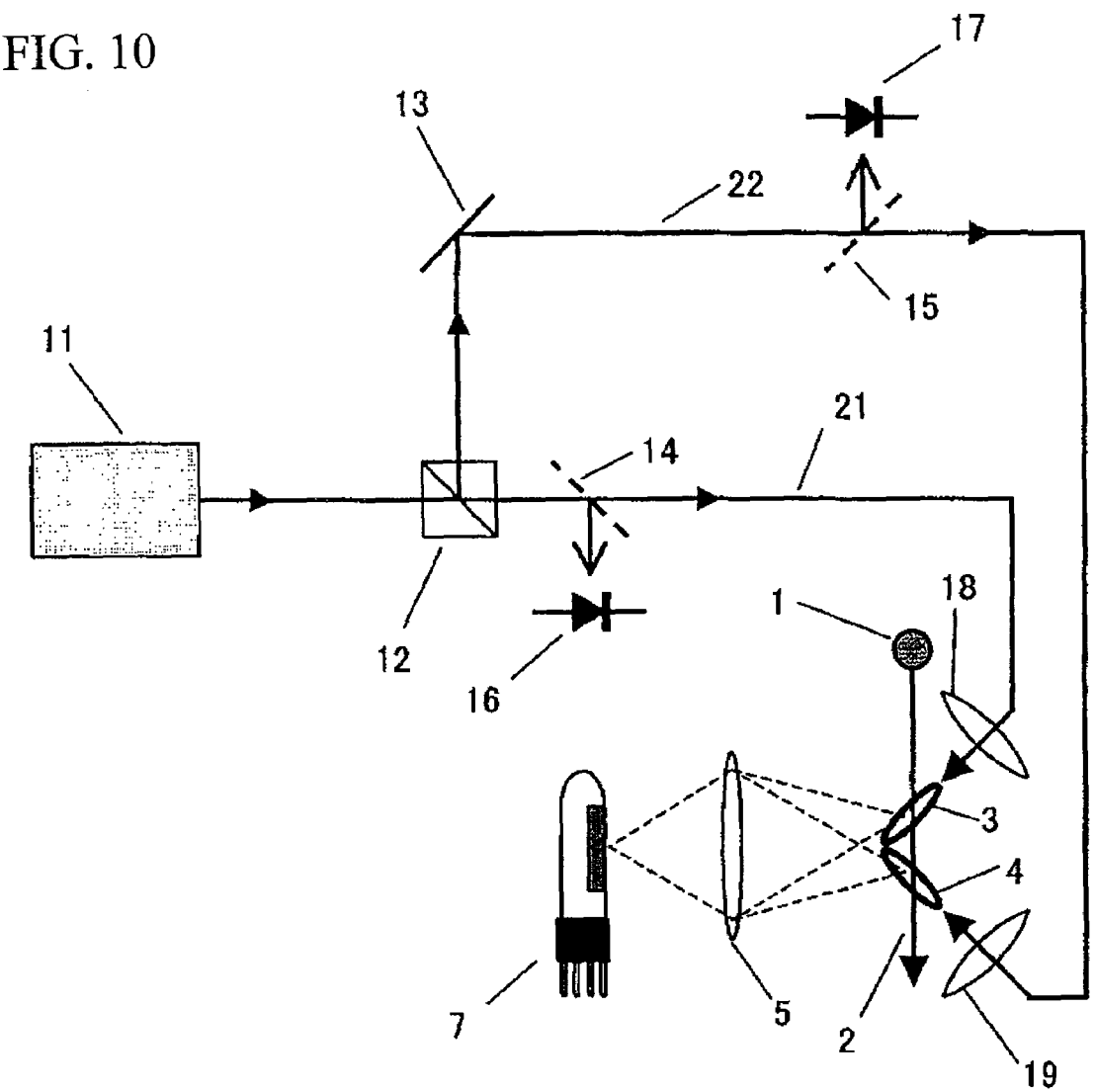
FIG. 10 is a schematic configuration view of a surface inspection apparatus according to a third embodiment of the present invention.

Next, a third embodiment of the present invention will be described. FIG. 10 is a schematic configuration view of a surface inspection apparatus according to the third embodiment of the present invention. In addition, parts in common with the first and the second embodiments of the present invention will not be described herein.

In FIG. 10, a light source 11 generates a pulse laser which performs pulse oscillation by time repeating, and a time interval of the pulse oscillation is a time interval which is set so that light emissions of a plurality of times are included within a time in which a contaminant particle 1 passes through an illumination spot by primary scan. Light emitted from the light source 11 is divided into two illumination beams 21 and 22 by a beam splitter 12.

The illumination beam 21 forms an illumination spot 3 shown in FIG. 4 by the function of the irradiation lens 18; and the illumination beam 22 forms an illumination spot 4 by the function of the irradiation lens 19. An optical path having a longer optical path length is configured so that the illumination beam 22 is irradiated to a wafer 100 with being delayed as compared with the illumination beam 21. Difference between the optical path lengths is configured so that a delay time corresponds to a time from 1/10 to 1/2 of the pulse oscillation interval of the light source 11.

Beam splitters 14 and 15 which are for taking out part of the illumination beams 21 and 22, and photodiodes 16 and 17 which convert a time change signal waveform of the beam of the taken out part to an electrical signal are provided in the optical paths of the illumination beams 21 and 22 as light emitting start timing signal generating units which are for taking out light emitting start timings of the respective laser beams as signals.

In order to correctly detect light emitting time difference between the two illumination spots 3 and 4, the two photodiodes 16 and 17 are arranged at positions located at the same distances from the illumination spots 3 and 4 sides when following backward the optical paths of the illumination beams 21 and 22.

Light emitting timing signals obtained from the photodiodes 16 and 17 have waveforms, for example, as shown in FIGS. 11(A) and 11(B). Characteristics of the illumination spots formed by the respective illumination beams are equivalent to the first embodiment.

Figure 11:
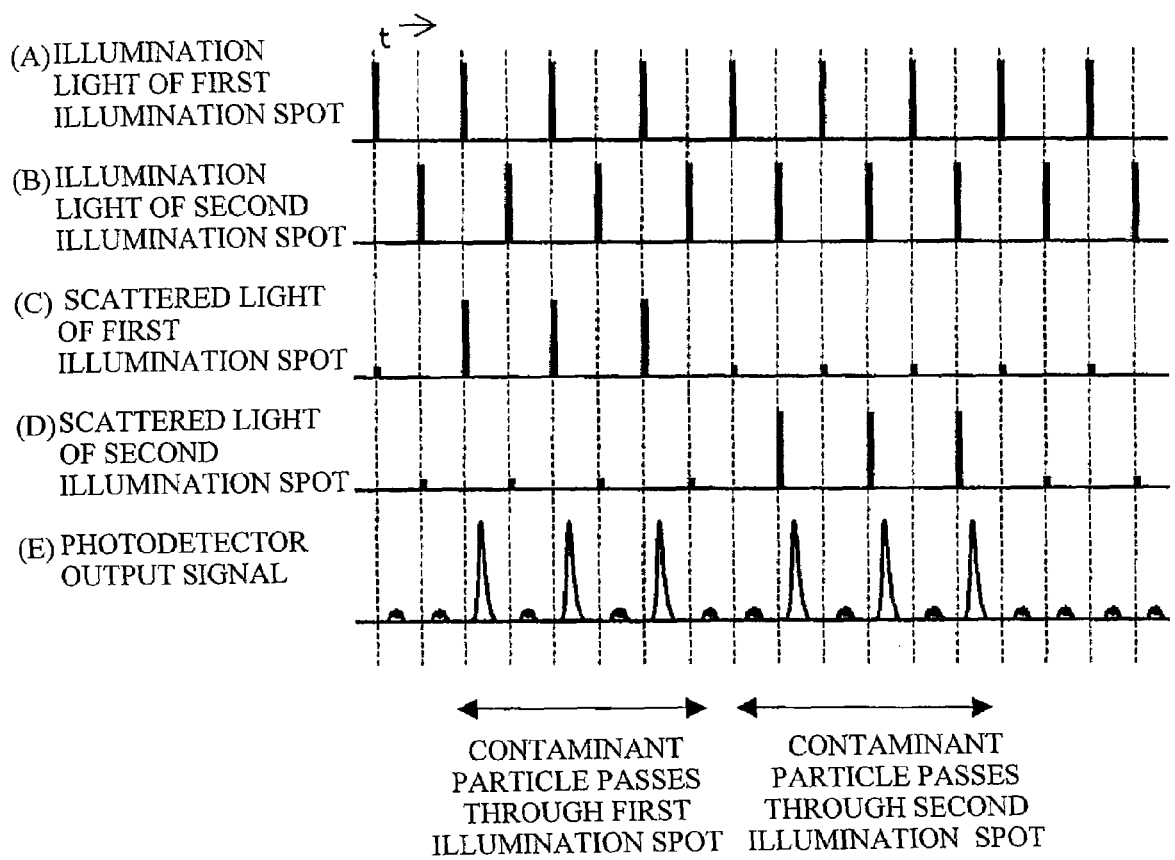
FIG. 11 is a view showing a light emitting timing of scattered light from an illumination spot according to the third embodiment of the present invention.

The contaminant particle 1 passes through the first illumination spot 3, and then, passes through the second illumination spot 4; and accordingly, scattered, diffracted, and reflected light signals can be obtained two times from a photodetector 7 (see FIGS. 11(C) and 11(D)). In this regard, however, since the light source 11 is a pulse laser, if time response speed of the photodetector 7 is sufficiently fast (this assumption is realistic enough for a photomultiplier), time intensity change of the scattered, diffracted, and reflected light signals generating during passing through the respective illumination spots 3 and 4 is not a continuous waveform; but, as shown in FIG. 11, the time intensity change is a discrete waveform corresponding to pulse oscillation of the light source 11.

As is apparent from FIGS. 11(C) and 11(D), to be exact, illumination light is not irradiated to the first illumination spot 3 and the second illumination spot 4 at the same time; and therefore, scattered, diffracted, and reflected lights from the first illumination spot 3 and scattered, diffracted, and reflected lights from the second illumination spot 4 are not generated at the same time.

In the third embodiment of the present invention, time instant and interval of time at which illumination light are actually irradiated to the respective illumination spots 3 and 4 can be exactly known by the former light emitting timing signal generating units (14, 15, 16, and 17). Consequently, if an output signal shown in FIG. 11(E) from the photodetector 7 is separated using the light emitting timing signal, it is possible to separate the scattered, diffracted, and reflected light signals from a plurality of the illumination spots 3 and 4 and to detect using one photodetector 7 only.

Figure 13:
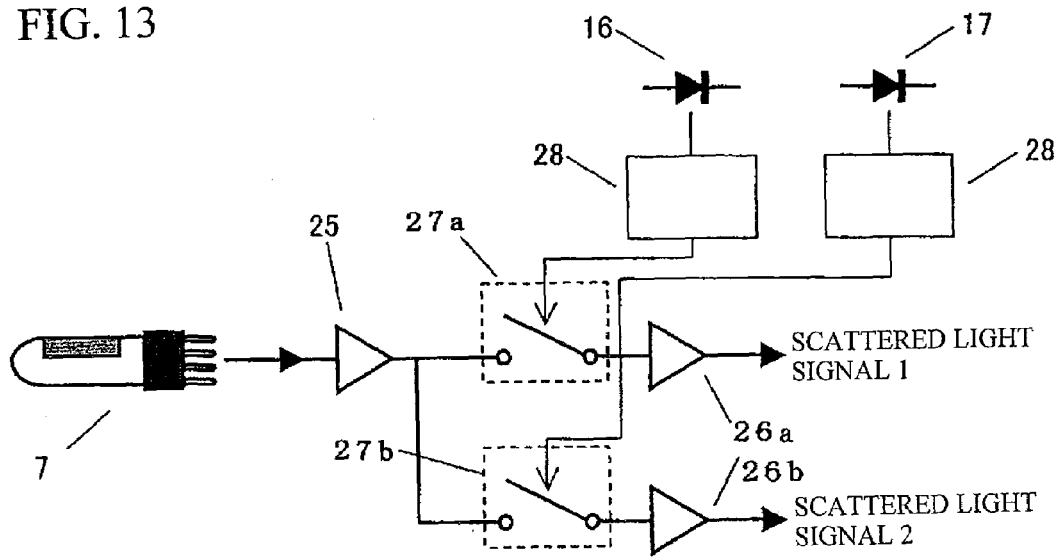
FIG. 13 is an explanation view for separating a signal by a separation circuit according to the third embodiment of the present invention.

More specifically, an output signal of the photodetector 7 is processed by a separation circuit having a configuration shown in FIG. 13. That is, the output signal of the photodetector 7 is amplified by a preamplifier 25, and then, distributed into two gate circuits 27a and 27b. ON and OFF operations of the respective gate circuits 27a and 27b are controlled in accordance with the light emitting timing signals from the photodiodes 16 and 17.

Figure 12:
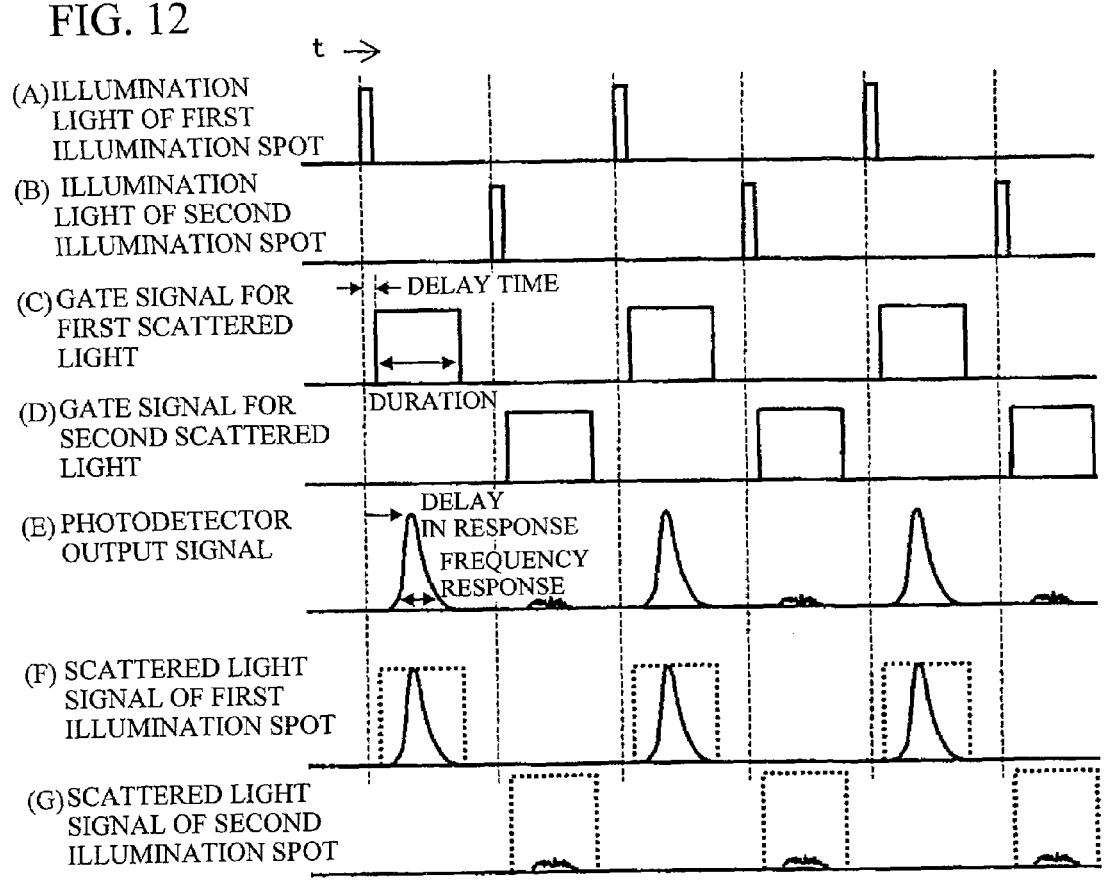
FIG. 12 is an explanation view of a gate signal generated from a light emitting start timing signal according to the third embodiment of the present invention.

As shown in FIG. 12(E), generally, the output signal of the photodetector 7 rises with being delayed with respect to light emitting timing of the illumination light 21 and 22, and frequency response speed is slow as compared with light emitting duration (for example, approximately 15 ps); and therefore, the pulse width of the output signal of the photodetector 7 becomes longer than the light emitting duration of the illumination light 3 and 4.

Consequently, a waveform shaper 28 is provided in order to give a predetermined delay time and a pulse duration to the light emitting timing signals from the photodiodes 16 and 17. Output signals from the waveform shaper 28 have waveforms as shown in FIGS. 12(C) and 12(D), for example. Scattered, diffracted, and reflected light signals corresponding to the respective illumination spots 3 and 4 shown in FIGS. 12(F) and 12(G) are separated from the output signal of the preamplifier 25 by performing ON and OFF operations of the gate circuits 27a and 27b by the gate signals from the waveform shapers 28. After that, the separated respective scattered, diffracted, and reflected light signals are further amplified by amplifiers 26a and 26b.

As described above, the scattered, diffracted, and reflected light signals corresponding to the plurality of the illumination spots 3 and 4 can be separated from the output signal of one photodetector 7 and detected by using the separation circuit shown in FIG. 13; and each of the separated and individual scattered, diffracted, and reflected light signals is not influenced by background light of the illumination spots 3 and 4 of not corresponding side.

In the case where the sum of the scattered, diffracted, and reflected light signals of two times is calculated to be total scattered, diffracted, and reflected light signals as in the first embodiment of the present invention; the magnitude of the total scattered, diffracted, and reflected light signals is two times as large as the scattered, diffracted, and reflected light signals in the case of using one illumination spot only.

In addition, since the separated and individual scattered, diffracted, and reflected light signals are influenced by only background scattered light from each one of the illumination spots, noise included in each of the scattered, diffracted, and reflected light signals is equivalent to the case where only one illumination spot is used; and the magnitude of noise included in the result taken from the sum of the scattered, diffracted, and reflected light signals of two times becomes square root of 2 times. As a result, since the total scattered, diffracted, and reflected light signal is two times and the noise is square root of 2 times; an S/N ratio is improved to square root of 2 times.

As described above, in the surface inspection apparatus according to the third embodiment of the present invention, there can be obtained an advantage that detection sensitivity is improved in addition to the effects obtained in the first or the second embodiment.

Figure 14:
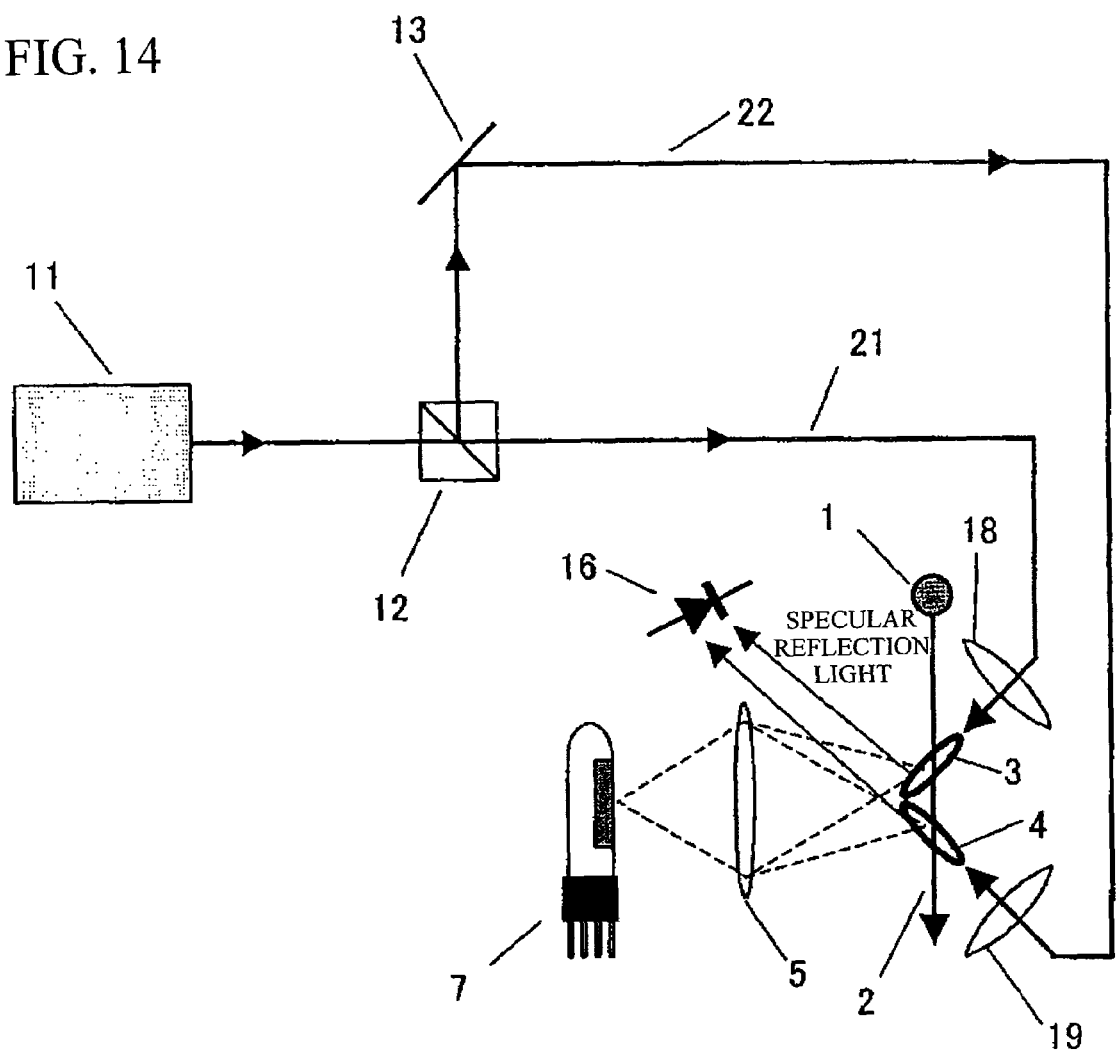
FIG. 14 is a schematic configuration view of a modified example of a surface inspection apparatus according to the third embodiment of the present invention.
Figure 15:
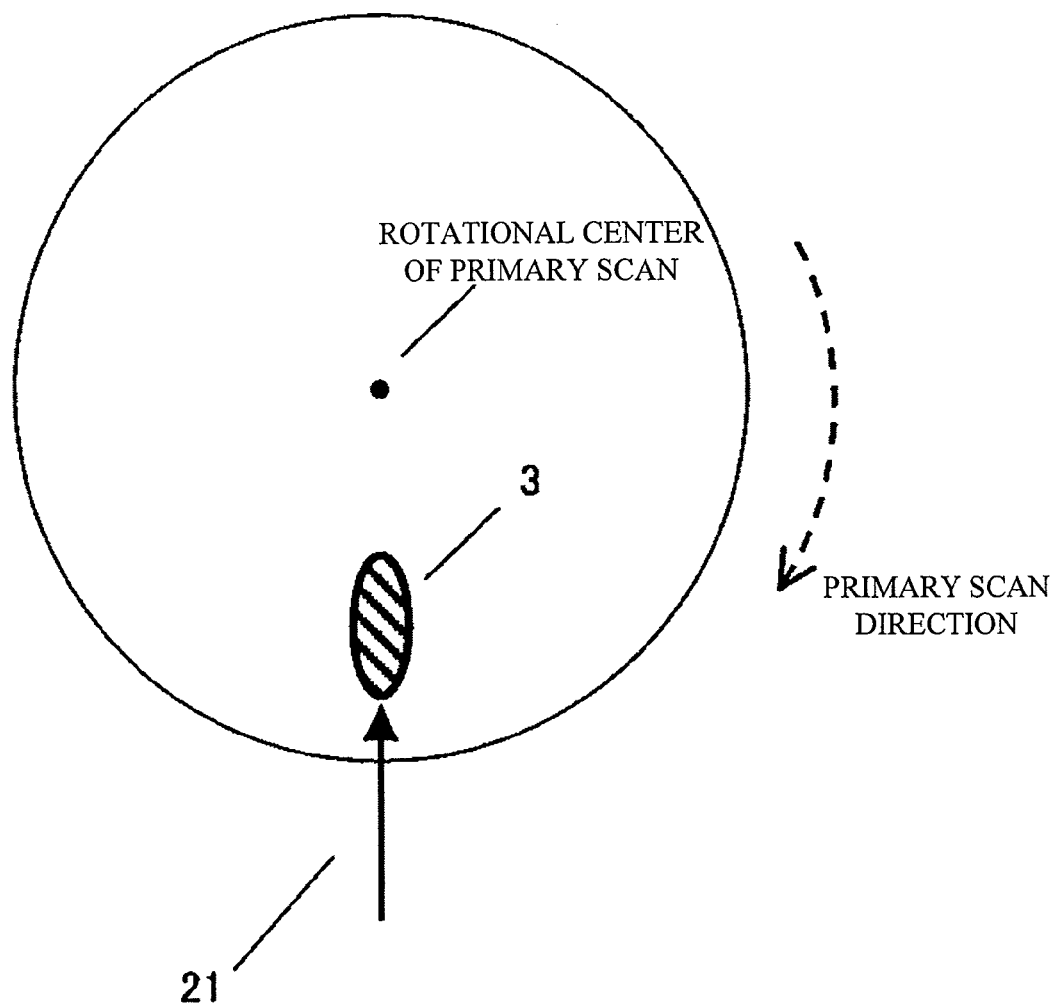
FIG. 15 is an explanation view in the case where a semiconductor wafer is illuminated from one azimuthal angle.
Figure 16:
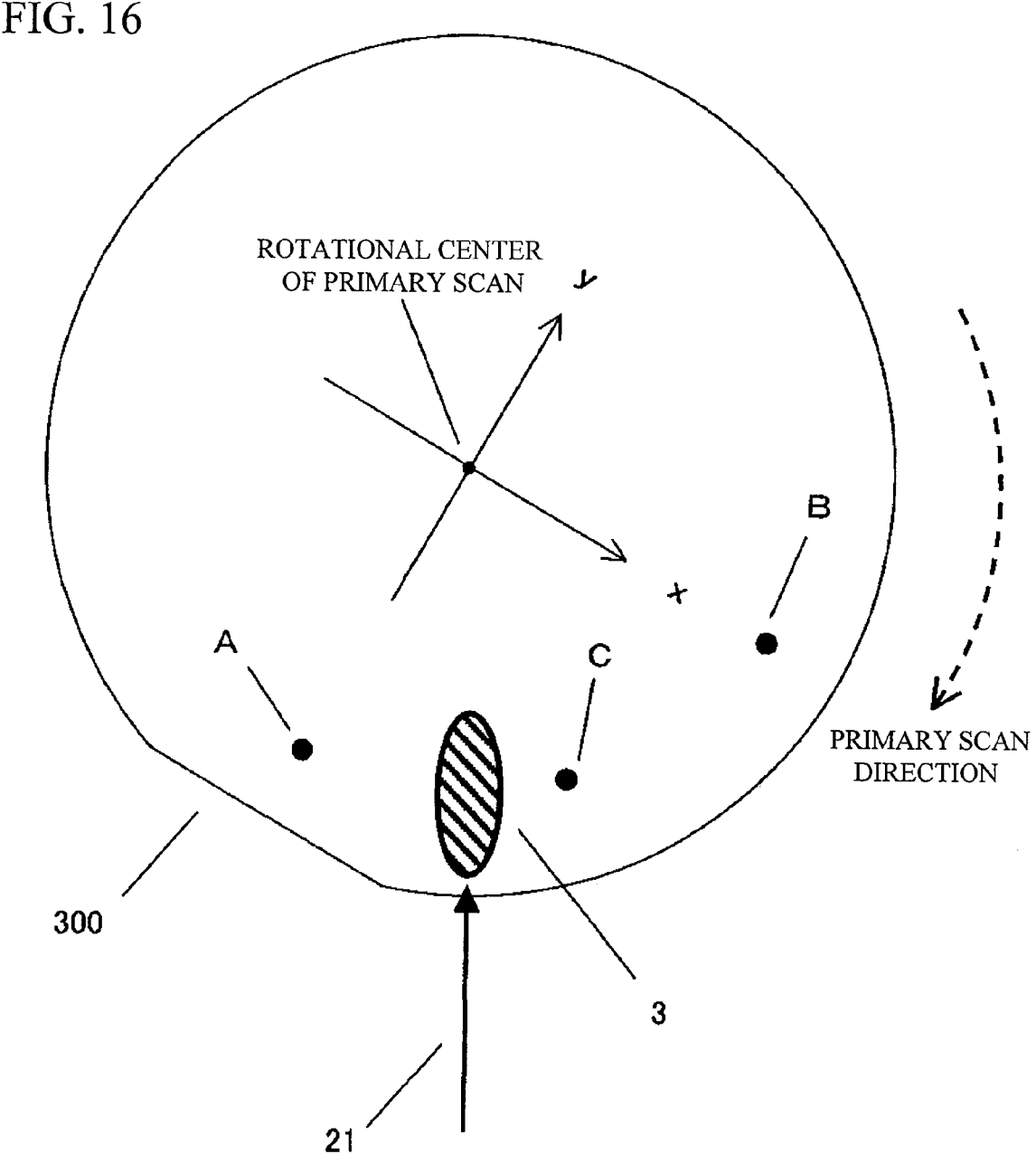
FIG. 16 is an explanation view in the case where a semiconductor wafer is illuminated from one azimuthal angle.
Figure 17:
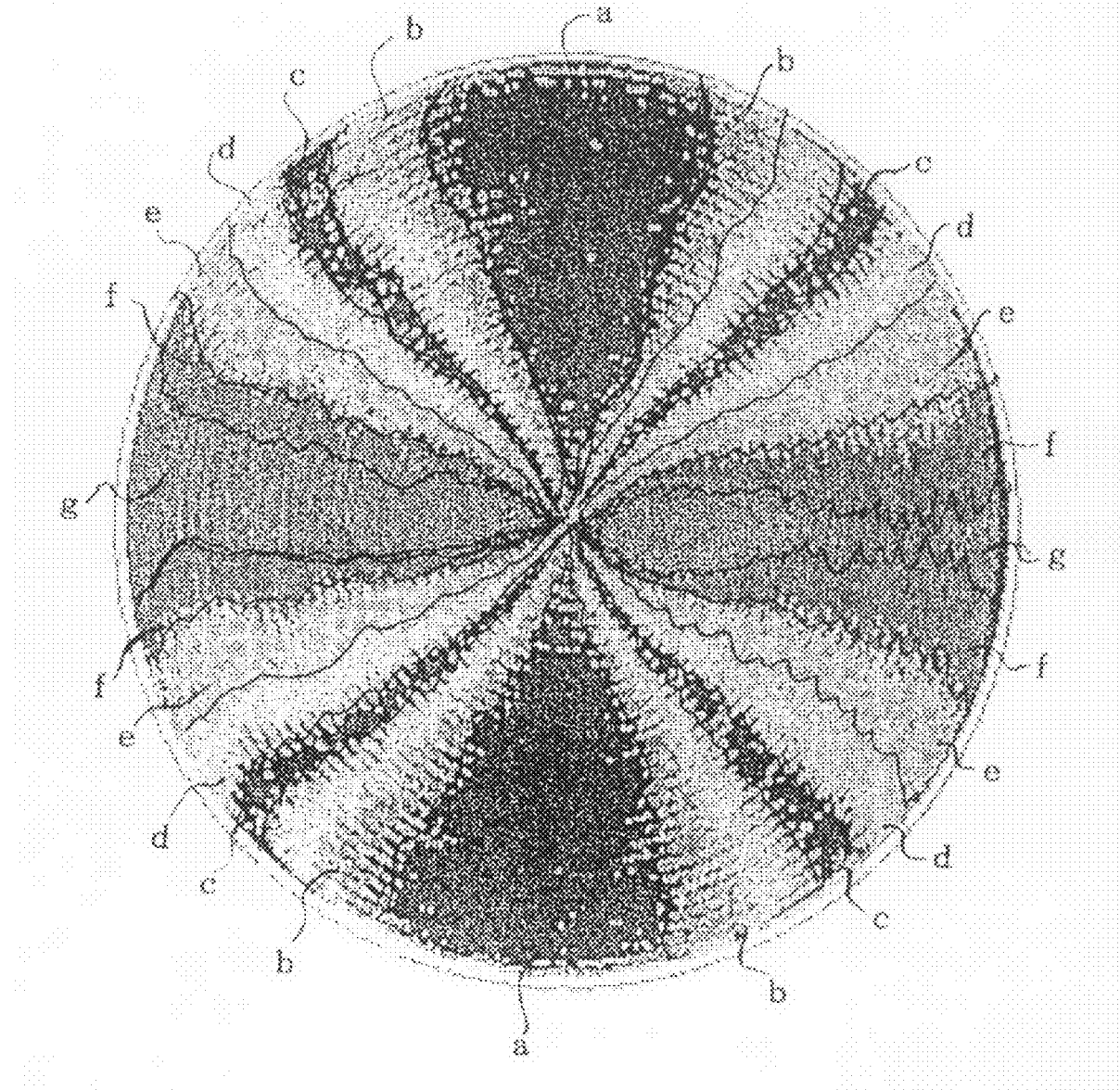
FIG. 17 is a view showing intensity distribution of a signal derived from surface roughness of the semiconductor wafer.

In the third embodiment of the present invention, light emitting timings of the two illumination beams 21 and 22 are optically monitored on the optical paths of the respective illumination beams 21 and 22; however, as shown in FIG. 14, this may be configured such that part of specular reflection light from two illumination spots 3 and 4 are optically monitored by the photodiode 16.

In addition, it may be generated on the basis of a light emitting synchronous signal outputted from the pulse laser source 11, or a light emitting control signal given to the pulse laser source 11 from outside for the control of the pulse laser source 11.

In this case, a delay time of a second illumination spot 4 having light emitting timing delayed with respect to the first illumination spot 3 may be previously obtained by calculation from difference between both optical path lengths. In addition, in place of giving the delay time between two illumination beams 21 and 22 by changing the optical path lengths of the illumination beams 21 and 22, there can be used a technology which separates an optical beam emitted from a pulse laser of the light source 11 into two optical beams different in pulse light emitting timing by passing the optical beam through an electro-optical (referred to as EO) modulator using Kerr effect or the like.

Generally, if a continuously oscillating laser beam is incident to an EO modulator and modulated by a suitable frequency signal, a first output beam in which an incident beam is intensity modulated by the above suitable frequency is obtained from one of two types of output beams; and from the other, an output beam inverted in phase with a first output beam, that is, inverted in level with the first output beam is obtained.

When an optical beam from the laser light source 11, which performs pulse oscillation, is incident to such EO modulator, the EO modulator is synchronized with a repetition rate of the light source 11, and appropriate phase difference is given to modulate; two output beams in which former pulse oscillation interval is two times, that is, the repetition rate is reduced to ½ can be obtained from two types of outputs of the EO modulator.

Then, oscillation timings of these two types of output beams are out of synchronization each other by the former oscillation interval of the incident beam; and therefore, this can be used in place of the technology "a delay time is given between two illumination beams by changing an optical path length."

As described above, according to the present invention, the surface of the object to be inspected is illuminated from two directions mutually different in the azimuthal angle by 90°, and scattered, diffracted, and reflected lights from both illumination lights are detected; accordingly, influence of anisotropy in which a contaminant particle or a defect existing in the object to be inspected itself or thereon possess with respect to an illumination direction, can be eliminated or reduced; and therefore, inspection of the aforementioned contaminant particle and defect or surface roughness can be achieved with substantially uniform sensitivity, without depending on a rotation angle in a primary scan direction.

What is claimed is:

1. An inspection method of a substrate before forming a pattern which irradiates an optical beam onto the surface of a substrate before forming the pattern mounted on a movement stage for the substrate before forming a pattern, in which primary scan is performed by rotational movement and secondary scan is performed by translation movement; comprising
    collecting scattered, diffracted, and reflected lights from the substrate before forming a pattern;
    and inspects the surface of the substrate before forming a pattern on the basis of the collected light, the inspection method of substrate before forming a pattern comprising the steps of:
    irradiating two optical beams from mutually different azimuthal angles at substantially the same elevation angles with respect to the surface of the substrate before forming a pattern, onto two regions different in the surface of the substrate before forming a pattern;
    collecting scattered, diffracted, and reflected lights from the two regions; and
    detecting the position and the size of a contaminant particle and a defect existing on the surface of the substrate before forming a pattern or in the inside adjacent to the surface, or surface roughness of the substrate before forming a pattern on the basis of the collected light.

2. The inspection method according to claim 1, further comprising the step of dividing optical beam generated from one light source into two optical beams.

3. The inspection method according to claim 2, wherein the two optical beams have extended lines which intersect with each other on a straight line passing through the center of the rotational movement.

4. The inspection method according to claim 3, wherein the extended lines of the two optical beams are intersected by an angle of approximately 90 degrees.

5. The inspection method according to claim 2, wherein the two optical beams are both p polarizations, both s polarizations, both circular polarizations, or both elliptical polarizations having substantially equivalent ellipticity.

6. The inspection method according to claim 1, further comprising the step of calculating the size of the contaminant particle and the defect existing on the surface of the substrate before forming a pattern or in the inside adjacent to the surface, or surface roughness of the substrate before forming a pattern on the basis of the sum of the scattered, diffracted, and reflected lights from the two regions.

7. A surface inspection method which irradiates an optical beam onto the surface of an object to be inspected mounted on a movement stage for the object to be inspected, in which primary scan is performed by rotational movement and secondary scan is performed by translation movement; collects scattered, diffracted, and reflected lights from the object to be inspected; and inspects the surface of the object to be inspected on the basis of the collected light, the surface inspection method comprising the steps of;
    irradiating two optical beams from mutually different azimuthal angles at substantially the same elevation angles with respect to the surface of the object to be inspected, onto two regions different in the surface of the object to be inspected;
    collecting scattered, diffracted, and reflected lights from the two regions; and
    detecting the position and the size of a contaminant particle and a defect existing on the surface of the object to be inspected or in the inside adjacent to the surface, or surface roughness of the object to be inspected on the basis of the collected light, the surface inspection method further comprising the step of collecting the scattered, diffracted, and reflected lights from the two regions by a condenser element which collects the scattered, diffracted, and reflected lights at substantially equivalent elevation angle with respect to the surface of the object to be inspected, and in four to six azimuth directions being mutually different with respect to a primary scan rotation axis of the movement stage for the object to be inspected and mutually spaced apart by approximately from not less than 60° to not more than 100°.

8. A surface inspection method which irradiates an optical beam onto the surface of an object to be inspected mounted on a movement stage for the object to be inspected, in which primary scan is performed by rotational movement and secondary scan is performed by translation movement; collects scattered, diffracted, and reflected lights from the object to be inspected; and inspects the surface of the object to be inspected on the basis of the collected light, the surface inspection method comprising the steps of;
    irradiating two optical beams from mutually different azimuthal angles at substantially the same elevation angles with respect to the surface of the object to be inspected, onto two regions different in the surface of the object to be inspected;
    collecting scattered, diffracted, and reflected lights from the two regions; and
    detecting the position and the size of a contaminant particle and a defect existing on the surface of the object to be inspected or in the inside adjacent to the surface, or surface roughness of the object to be inspected on the basis of the collected light;
    the surface inspection method further comprising the steps of:
    dividing optical beam generated from one light source into two optical beams;
    generating a pulse laser by the one light source;
    setting an optical path length of a first optical beam divided from the pulse laser from the light source to a first region of the two regions different in the surface of the object to be inspected shorter than an optical path length of a second optical beam divided from the pulse laser from the light source to a second region of the two regions different in the surface of the object to be inspected; and
    setting a delay time by setting a time from when the second optical beam is emitted from the light source and divided until reaching the second region longer than a time from when the first optical beam is emitted from the light source and divided until reaching the first region.

9. The surface inspection method according to claim 8, wherein the delay time, which is difference between the time which the second optical beam takes to reach the second region and the time when from the first optical beam is emitted from the light source and divided until reaching the first region, is set to a range of approximately ¹/₁₀ to ½ of a pulse laser repetition period of the light source.

10. The surface inspection method according to claim 8, further comprising the steps of:
    collecting the scattered, diffracted, and reflected lights from the first region and the scattered, diffracted, and reflected lights from the second region by one condenser unit; and
    detecting by separating the scattered, diffracted, and reflected lights from the first region from the scattered, diffracted, and reflected lights from the second region on the basis of the delay time.

11. An inspection apparatus of a substrate before forming a pattern including a movement stage for a substrate forming a pattern, in which primary scan is performed by rotational movement and secondary scan is performed by translation movement;
    a unit which irradiates an optical beam onto the surface of the substrate before forming a pattern mounted on the stage;
    a unit which collects scattered, diffracted, and reflected lights from the substrate before forming a pattern; and an inspection unit which inspects the surface of the substrate before forming a pattern on the basis of the collected light, the inspection apparatus of a substrate before forming a pattern, comprising:
    an optical beam irradiating unit which irradiates two optical beams from mutually different azimuthal angles at substantially the same elevation angles with respect to the surface of the substrate before forming a pattern, onto two regions different in the surface of the substrate before forming a pattern;
    a condenser unit which collects scattered, diffracted, and reflected lights from the two regions; and
    a detecting unit which detects the position and the size of a contaminant particle and a defect existing on the surface of the substrate before forming a pattern or in the inside adjacent to the surface, or surface roughness of the substrate before forming a pattern on the basis of the collected light.

12. The inspection apparatus according to claim 11, wherein the optical beam irradiating unit includes one light source; and a unit which divides an optical beam generated from the one light source into two optical beams.

13. The inspection apparatus according to claim 12, wherein the optical beam irradiating unit makes extended lines of the two optical beams intersect with each other on a straight line passing through the center of the rotational movement.

14. The inspection apparatus according to claim 13, wherein the extended lines of the two optical beams are intersected by an angle of approximately 90 degrees.

15. The inspection apparatus according to claim 12, further comprising a polarization unit which polarizes the two optical beams to both p polarizations, both s polarizations, both circular polarizations, or both elliptical polarizations having substantially equivalent ellipticity.

16. The inspection apparatus according to claim 11, wherein the inspection unit calculates the size of the contaminant particle and the defect existing on the surface of the substrate before forming a pattern or in the inside adjacent to the surface, or surface roughness of the substrate before forming a pattern on the basis of the sum of the scattered, diffracted, and reflected lights from the two regions.

17. A surface inspection apparatus including a movement stage for an object to be inspected, in which primary scan is performed by rotational movement and secondary scan is performed by translation movement: a unit which irradiates an optical beam onto the surface of the object to be inspected mounted on the stage; a unit which collects scattered, diffracted, and reflected lights from the object to be inspected; and an inspection unit which inspects the surface of the object to be inspected on the basis of the collected light, the surface inspection apparatus comprising;
    an optical beam irradiating unit which irradiates two optical beams from mutually different azimuthal angles at substantially the same elevation angles with respect to the surface of the object to be inspected, onto two regions different in the surface of the object to be inspected;
    a condenser unit which collects scattered, diffracted, and reflected lights from the two regions; and
    a detecting unit which detects the position and the size of a contaminant particle and a defect existing on the surface of the object to be inspected or in the inside adjacent to the surface, or surface roughness of the object to be inspected on the basis of the collected light,
    the surface inspection apparatus further comprising a condenser element which collects the scattered, diffracted, and reflected lights, the condenser element collecting the scattered, diffracted, and reflected lights from the two regions at substantially equal elevation angle with respect to the surface of the object to be inspected, and in four to six azimuth directions being mutually different with respect to a primary scan rotation axis of the movement stage for the object to be inspected and being mutually spaced apart by approximately from not less than 60° to not more than 100°.

18. A surface inspection apparatus including a movement stage for an object to be inspected, in which primary scan is performed by rotational movement and secondary scan is performed by translation movement; a unit which irradiates an optical beam onto the surface of the object to be inspected mounted on the stage; a unit which collects scattered, diffracted, and reflected lights from the object to be inspected; and an inspection unit which inspects the surface of the object to be inspected on the basis of the collected light. the surface inspection apparatus comprising;
    an optical beam irradiating unit which irradiates two optical beams from mutually different azimuthal angles at substantially the same elevation angles with respect to the surface of the object to be inspected, onto two regions different in the surface of the object to be inspected;
    a condenser unit which collects scattered, diffracted, and reflected lights from the two regions; and
    a detecting unit which detects the position and the size of a contaminant particle and a defect existing on the surface of the object to be inspected or in the inside adjacent to the surface, or surface roughness of the object to be inspected on the basis of the collected light,
    wherein the optical beam irradiating unit includes one light source; and a unit which divides an optical beam generated from the one light source into two optical beams;
    the surface inspection apparatus further comprising:
    generating a pulse laser by the one light source;

setting an optical path length of a first optical beam divided from the pulse laser from the light source to a first region of the two regions different in the surface of the object to be inspected shorter than an optical path length of a second optical beam divided from the pulse laser from the light source to a second region of the two regions different in the surface of the object to be inspected; and setting a delay time by setting a time from when the second optical beam is emitted from the light source and divided until reaching the second region longer than a time from when the first optical beam is emitted from the light source and divided until reaching the first region.

19. The surface inspection apparatus according to claim 18, wherein the delay time, which is difference between the time which the second optical beam takes to reach the second region and the time from when the first optical beam is emitted from the light source and divided until reaching the first region, is set to a range of approximately 1/10 to 1/2 of a pulse laser repetition period of the light source.

20. The surface inspection apparatus according to claim 18, further comprising:

collecting the scattered, diffracted, and reflected lights from the first region and the scattered, diffracted, and reflected lights from the second region by one condenser unit; and detecting by separating the scattered, diffracted, and reflected lights from the first region from the scattered, diffracted, and reflected lights from the second region on the basis of the delay time.

* * * * *